US009808285B2

(12) United States Patent
Anderson

(10) Patent No.: US 9,808,285 B2
(45) Date of Patent: Nov. 7, 2017

(54) ASYMMETRICAL DUAL PROXIMAL END INSERTION BELLOW

(71) Applicant: Robert G. Anderson, Aledo, TX (US)

(72) Inventor: Robert G. Anderson, Aledo, TX (US)

( * ) Notice: Subject to any disclaimer, the term of this patent is extended or adjusted under 35 U.S.C. 154(b) by 0 days.

(21) Appl. No.: 15/179,983

(22) Filed: Jun. 11, 2016

(65) Prior Publication Data

US 2016/0278808 A1    Sep. 29, 2016

(51) Int. Cl.
*A61F 2/12* (2006.01)
*A61B 17/34* (2006.01)
*A61F 2/00* (2006.01)
*A61B 17/00* (2006.01)

(52) U.S. Cl.
CPC ........ *A61B 17/3468* (2013.01); *A61F 2/0095* (2013.01); *A61F 2/12* (2013.01); *A61B 2017/00792* (2013.01)

(58) Field of Classification Search
CPC ......... A61F 2/12; A61L 27/18; A61L 2430/04
See application file for complete search history.

(56) References Cited

U.S. PATENT DOCUMENTS

| | | |
|---|---|---|
| 4,641,648 A | 2/1987 | Shapiro |
| 4,955,906 A | 9/1990 | Coggins et al. |
| 5,199,795 A | 4/1993 | Russo et al. |
| 5,571,178 A | 11/1996 | Ledergerber |
| 5,723,006 A | 3/1998 | Ledergerber |
| 5,782,913 A | 7/1998 | Schindler et al. |
| 8,206,443 B2 | 6/2012 | Preissman |
| 8,211,173 B2 | 7/2012 | Keller et al. |
| 8,313,760 B2 | 11/2012 | Hunter |
| 8,550,090 B2 | 10/2013 | Keller et al. |
| 8,555,893 B2 | 10/2013 | Keller et al. |
| 8,641,758 B1 | 2/2014 | Anderson |
| D738,490 S | 9/2015 | Anderson |
| 2007/0276484 A1 | 11/2007 | Abell et al. |
| 2009/0204107 A1 | 8/2009 | Keller et al. |
| 2010/0280610 A1 | 11/2010 | Preissman |

(Continued)

FOREIGN PATENT DOCUMENTS

| | | |
|---|---|---|
| CA | 2861438 A1 | 8/2013 |
| WO | WO/2013/122568 A1 | 8/2013 |

OTHER PUBLICATIONS

Richard A. Mladick, M.D., F.A.C.S. "No-Touch" Submuscular Saline Breast Augmentation Technique, Aesthetic Plastic Surgery, 17:183-192, 1993, New York, NY.

(Continued)

*Primary Examiner* — Thomas J Sweet
*Assistant Examiner* — Tiffany Shipmon
(74) *Attorney, Agent, or Firm* — Kirby B. Drake; Klemchuk LLP

(57) ABSTRACT

An apparatus and method for inserting prosthesis implants into a patient pocket. The apparatus has three openings including a prosthesis opening, a large proximal opening, and a small proximal opening. The apparatus prevents infection; eases insertion and placement; and reduces complications. In use, the bellow is placed through the patient incision while allowing the bellow to be manipulated to force the prosthesis into a surgical pocket of a patient. Then the bellow is rotated so the distal end becomes the proximal end and inserted into the second incision while allowing the bellow to be manipulated to force the prosthesis into the second pocket.

3 Claims, 11 Drawing Sheets

(56) References Cited

U.S. PATENT DOCUMENTS

Figure 1:
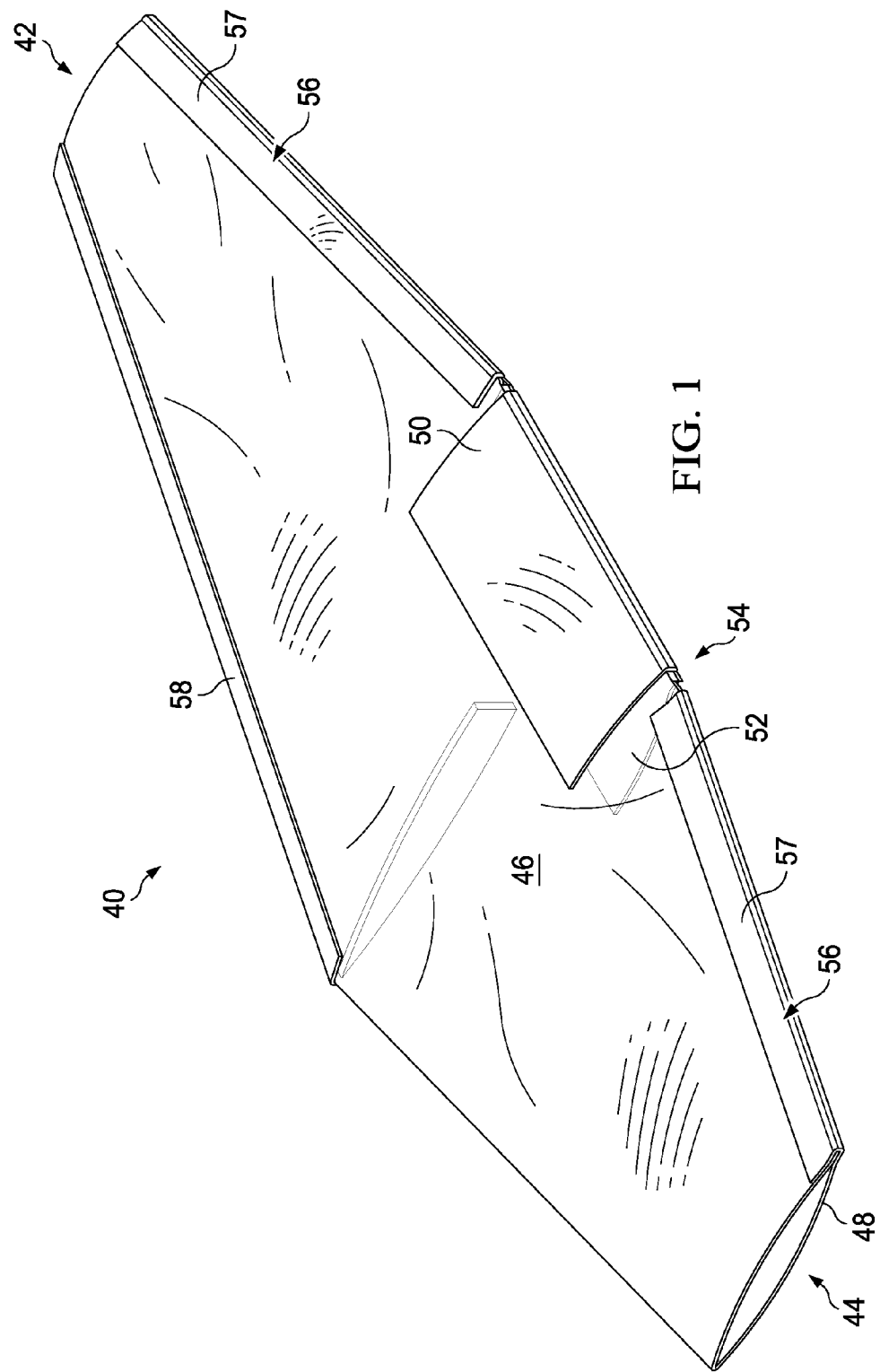

| | | |
|---|---|---|
| 2011/0035003 A1 | 2/2011 | Preissman |
| 2011/0218624 A1 | 9/2011 | Preissman |
| 2012/0185042 A1 | 7/2012 | Preissman |
| 2012/0259414 A1 | 10/2012 | Preissman |
| 2013/0073040 A1 | 3/2013 | Preissman |
| 2014/0074235 A1 | 3/2014 | Keller et al. |
| 2014/0074236 A1 | 3/2014 | Keller et al. |
| 2014/0148901 A1 | 5/2014 | Anderson |
| 2015/0374478 A1 | 12/2015 | Anderson |
| 2016/0038275 A1 | 2/2016 | Preissman |
| 2016/0095697 A1 | 4/2016 | Anderson |
| 2016/0278808 A1 | 9/2016 | Anderson |

OTHER PUBLICATIONS

Richard A. Mladick, M.D., F.A.C.S. Significance of *Staphylococcus epidermidis* Causing Subclinical Infection, Plastic & Reconstructive Surgery: Apr. 15, 2005—vol. 115—Issue 5—pp. 1426-1427, Virginia Beach, VA.

'Richard A. Mladick, M.D., F.A.C.S. Prevention of Capsular Contracture, Plastic & Reconstructive Surgery: May 1999—vol. 103—Issue 6—pp. 1773-1774, Virginia Beach, VA'.

Thomas M. Biggs, M.D. Prefilled Saline Breast Implants Offer Significant Advantages, Aesthetic Surgery Journal Sep. 1999 vol. 19 No. 5 424, St Louis, MO.

"Mitchel H. Brown, M.D.., M.Ed. Cohesive Silicone Gel Breast Implants in Aesthetic and Reconstructive Breast Surgery,Plastic & Reconstructive Surgery: Sep. 1, 2005—vol. 116—Issue 3—pp. 768-779".

"International Search Report," for PCT Patent Application No. PCT/US17/16255, dated Jun. 28, 2017, 5 pages.

"Written Opinion of the International Search Authority," for PCT Patent Application No. PCT/US17/16255, dated Jun. 28, 2017, 9 pages.

Shaa'ista Ameen, "'No-Touch' Breast-Implant Insertion Device," University of Cape Town, Department of Human Biology, MSc (Med) Thesis, submitted Jan. 2016, 123 pages.

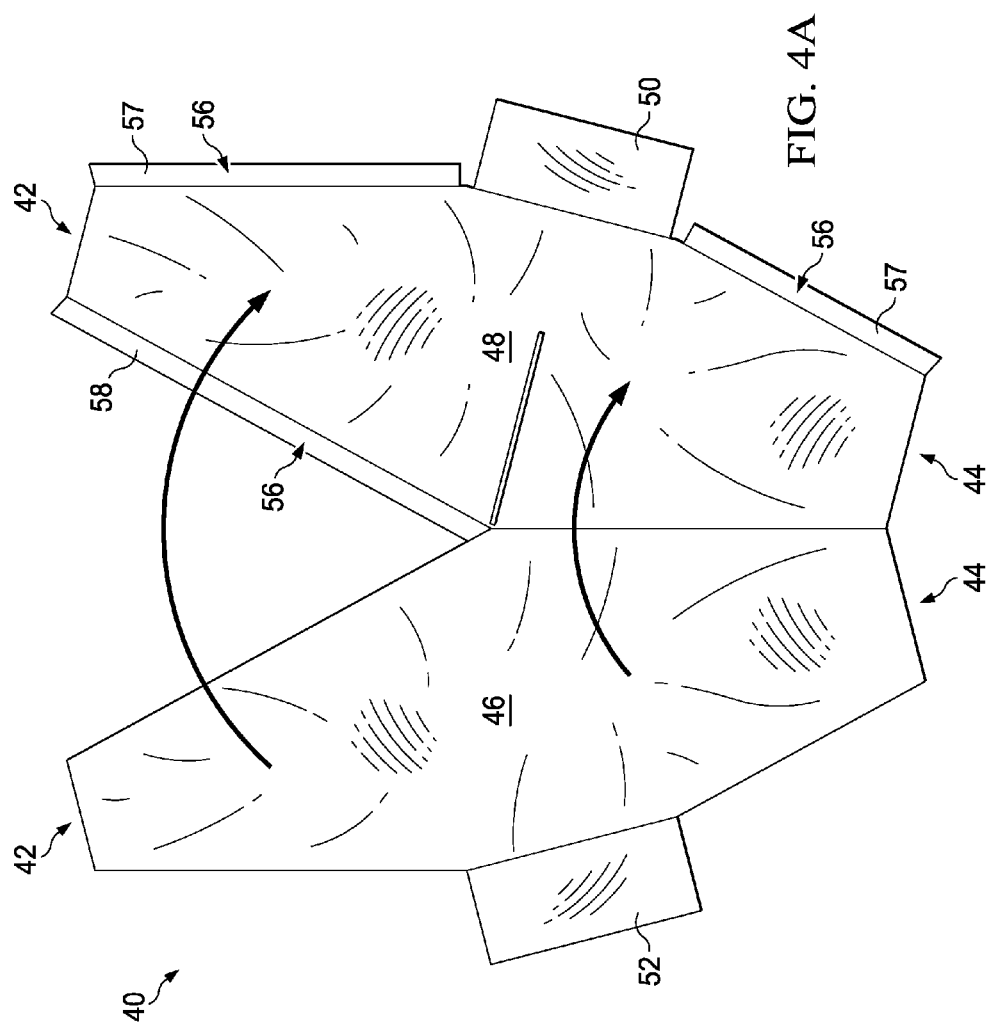

ASYMMETRICAL DUAL PROXIMAL END INSERTION BELLOW

CROSS-REFERENCE TO RELATED APPLICATIONS

This application claims priority to provisional application Ser. No. 62/348,338 entitled "Opposing Proximal Insertion Ends Implant Devices" filed on Jun. 10, 2016, the disclosures of which is hereby incorporated by reference in its entirety.

BACKGROUND

Field of Invention

These inventions relate to the apparatus and method of safely inserting a prosthesis into a human body.

Background of the Invention

The present inventions are useful and novel apparatuses for advancing breast implant surgery procedures to improve surgical sterility.

Breast implants are a manufactured prosthesis used in cosmetic and reconstructive surgery. A breast implant has an outer casing or membrane that is filled a fluid such as saline or a gelatinous cohesive silicone.

Only about thirty percent (30%) of breast implant procedures today use an insertion device. An insertion device improves both the surgery and the patient outcome. Without an insertion device, the surgeon makes the incision, creates a pocket for the implant, retracts the incision and then manually pushes the implant into the pocket.

Different than a silicone implant, a saline implant is inserted into the pocket in an empty configuration. Once placed in the pocket, the surgeon takes the additional step of filling the membrane with a saline solution using a tube.

The incision is made in one of four places: in the armpit, in the breast fold, in the navel, or around the areola. Except for the navel insertion, one incision is made for each implant. It is preferable that the incision be as short as possible. Shorter incisions are less unsightly. This goal of a shorter incision is easier to accomplish with a saline implant. A saline implant is relatively easy to insert through a short incision, as the bladder is unfilled and therefore small in size as it passes through the incision. For these inflatable implants, the surgeon rolls up the implant like a cigar and pushes it through the incision and into the pocket. In contrast, silicone implants are prefilled resulting in a more difficult and complications-susceptible operation. For these pre-filled implants, the procedure requires a longer incision length.

After the initial incisions, the surgeon dissects a path through the tissue to the desired destination of the implant. Once that path has been created, a pocket is created for the implant superficial or deep to the pectoralis major muscle. The pocket may be formed in one of two places under the breast: subglandular (between the breast tissue and pectoralis major muscle) or subpectoral (under the pectoralis major muscle). Subglandular places the prosthesis directly behind the mammary gland and in front of the muscle. Subpectoral places the implant partially under the pectoralis major muscle. Due to the structure of the pectoralis major muscle, a portion of the implant is not covered by the muscle.

A secondary surgery is common for patients with breast implants. In particular, patients with breast implants may require surgery to change the placement (from subglandular to subpectoral or vice versa), correct palpable folding of the implant, remove a ruptured implant; treat infection, bleeding, breast pain, contracted scar tissue forming around the implant and collections of fluid around the implant. These additional surgeries have risks due to anesthesia, infection and bleeding. The overall secondary operation complication rate is about 20% for silicone gel breast augmentation within 3 years of the initial operation and up to 36-45% by 10 years from the initial breast implant surgery. The majority of re-operations are related to implant rupture (leakage), bleeding or capsular contracture.

Cellulitis, a skin-based infection, occurs in 2%-4% of patients, with some surgeons reporting much higher rates, and is usually from the bacteria normally present on the skin. Symptoms of infection include fever, pain, swelling and redness. To reduce infection, surgeons give a single dose of antibiotics before the surgery, and use an antibiotic solution in the wound before implant placement. The antibiotic solution may double as the lubrication to allow easier insertion of the implant into the pocket. However, surgeons can bring the rate of capsular contracture and infection down further by preventing the implant from touching the patient's skin.

The implant insertion devices heretofore known suffer from a number of disadvantages:
1. The surgeon uses a single proximal end to insert both implants exposing the second incision to bacterial contamination from the insertion device proximal end touching the skin of the initial (first) incision and delivering bacteria into the second incision resulting in cellulitis, infection and or capsular contraction.
2. Requires the surgeon to resize the insertion device mid-operation to match two different implant sizes.
3. Relies on the correctly sized trimming by the surgeon. The implant company and insertion device company have no control over the surgeon. If the surgeon does not alter the device properly, unsafe damaging pressure may be applied to the implant during the insertion process.
4. Distal end of the device is large enough for the implant to inadvertently slip out of the device resulting in skin bacteria transferring to the implant.
5. The high cost of current implant devices encourages re-use despite the manufacturer recommendation not to do so.

SUMMARY OF THE INVENTION

An invention, which meets the needs stated above, is a system and method to insert two prostheses into a patient with maximum sterility. The method allows the surgeon to use two different size implants with a single device where each proximal end of the device receives a different size implant.

Objects and Advantages

Accordingly, besides the objects and advantages of the system for a breast implant insertion device described above, several objects and advantages of the present invention are:
a) to provide the means to further improve sterility by preventing the device end from touching the patient's skin and then being inserted into a second incision;

b) to provide a device for a procedure using two different size implants;
c) to provide a simplified insertion method;
d) to provide the means to reduce anesthesia time;
e) to provide a device that does not have to be trimmed by the surgeon;
f) to provide a single device that fits all sizes of implants;
g) to provide an easier manipulation of the implant.

Further objects and advantages of this invention will become apparent from a consideration of the drawings and the ensuing description of the drawings.

DRAWING FIGURES

The accompanying drawings, which are incorporated in and constitute a part of this specification, illustrate embodiments of the present invention and together with the description, serve to explain the principles of this invention. In the figures:

FIG. 1: Top side perspective view of an asymmetrical bellow divided by a baffle.

Figure 2:
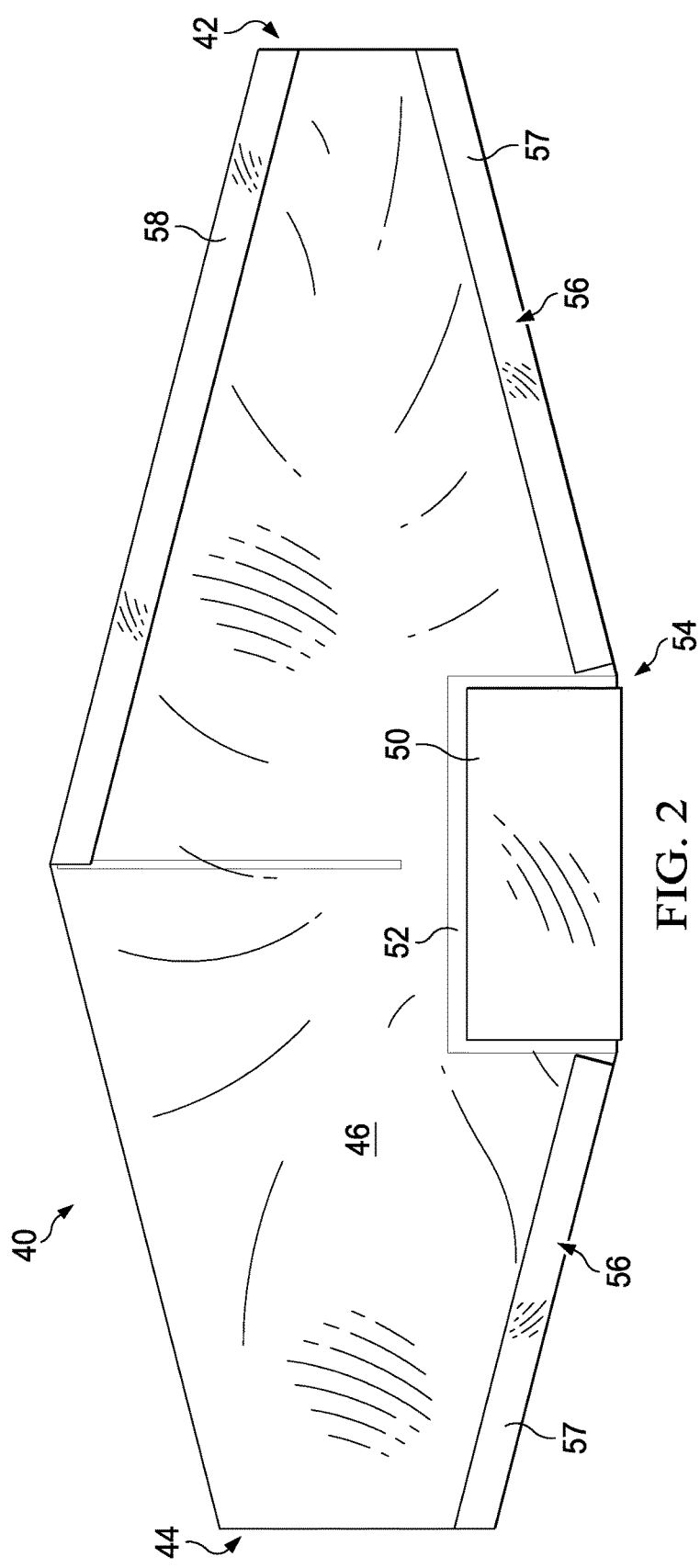

FIG. 2: Bottom view of an asymmetrical bellow with dual chambers separated by a baffle.

Figure 3:
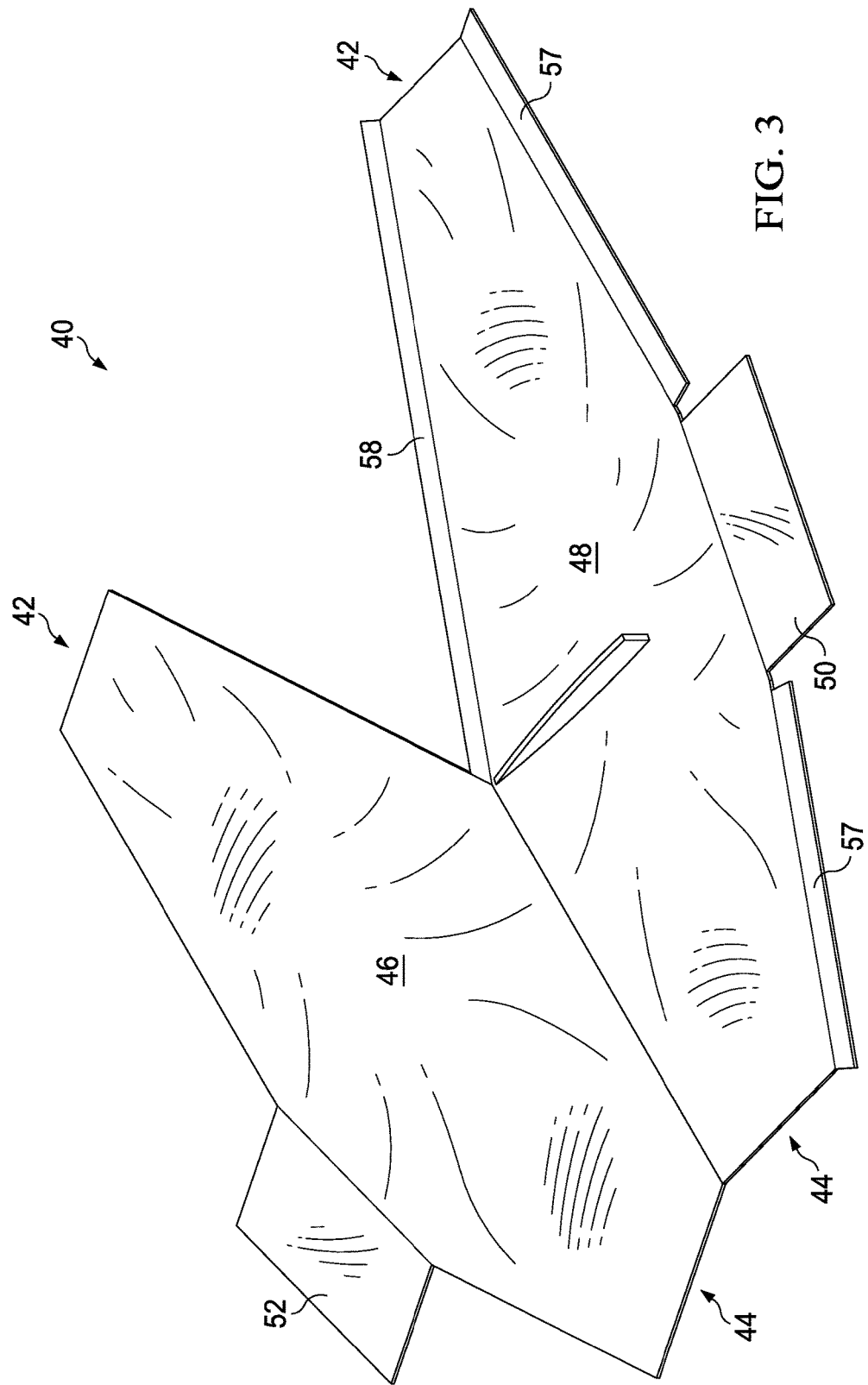

FIG. 3: Top side perspective view of an unassembled asymmetrical bellow with a baffled attached to the initial fold.

FIG. 4A: Top view of an unassembled asymmetrical bellow folded along the abutted edges.

Figure 4B:
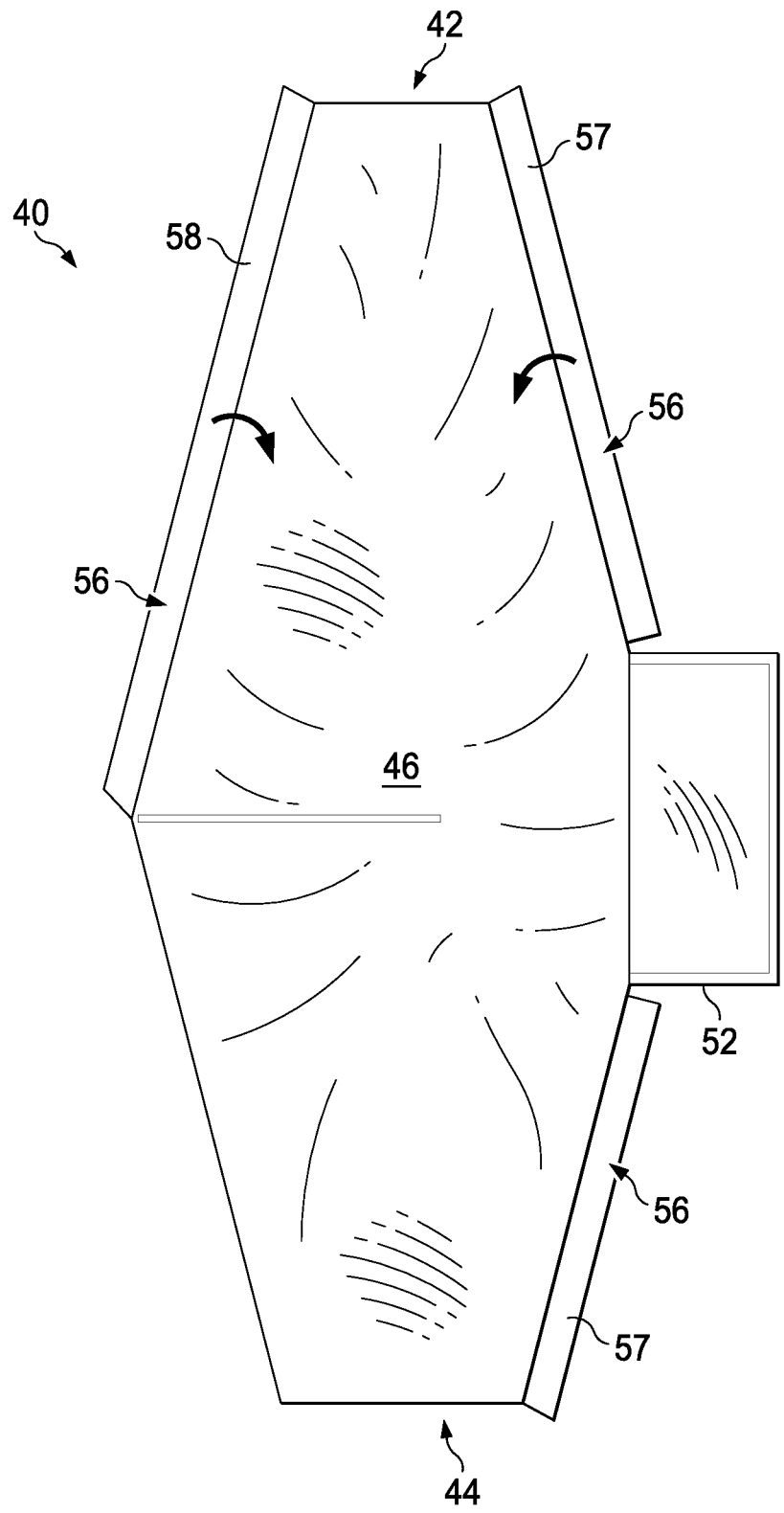

FIG. 4B: Top view of an asymmetrical bellow showing the base fold assembled over the initial fold.

Figure 4C:
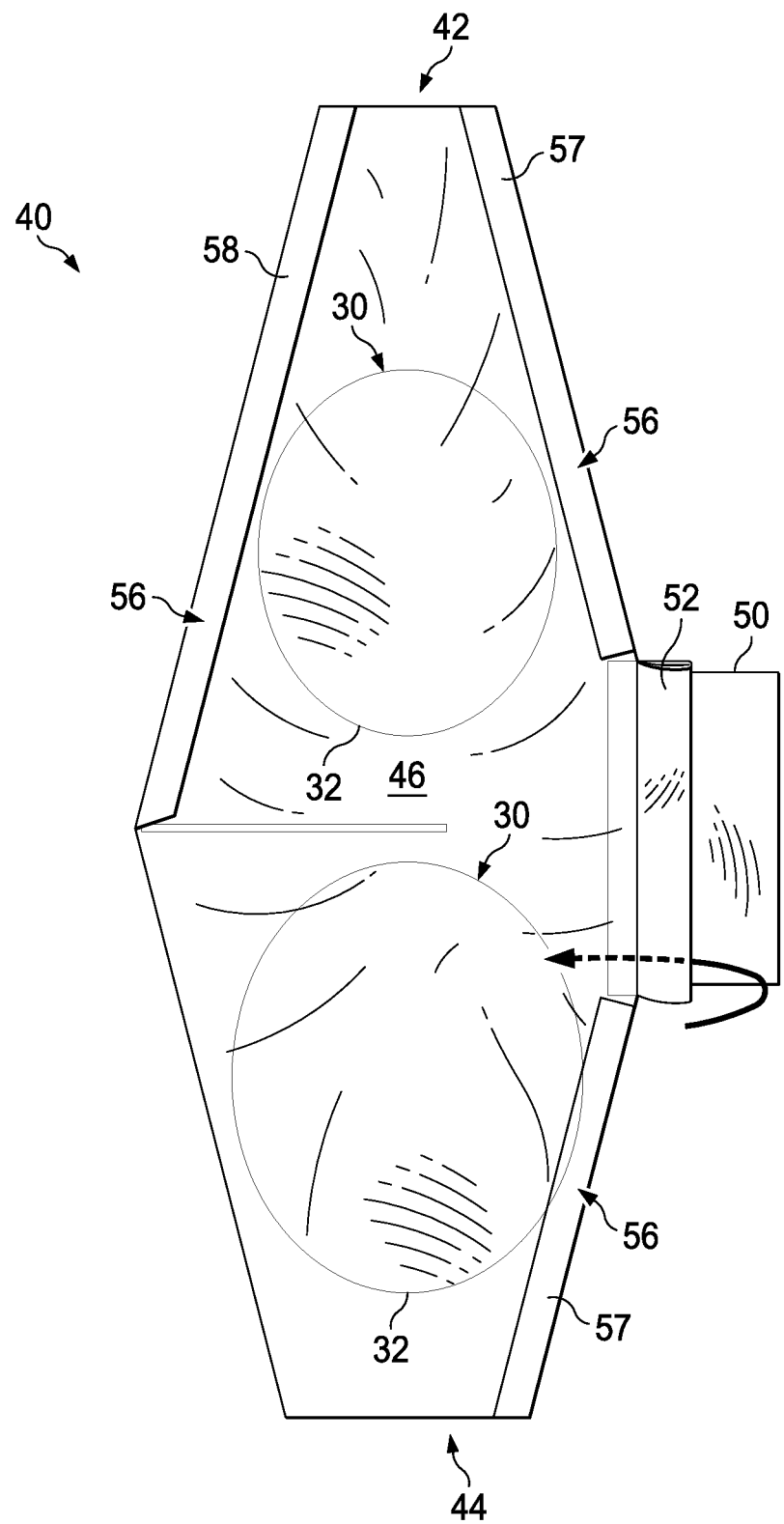

FIG. 4C: Top view of an asymmetrical bellow with the internal tab folded through prosthesis opening after the prostheses are inserted.

Figure 4D:
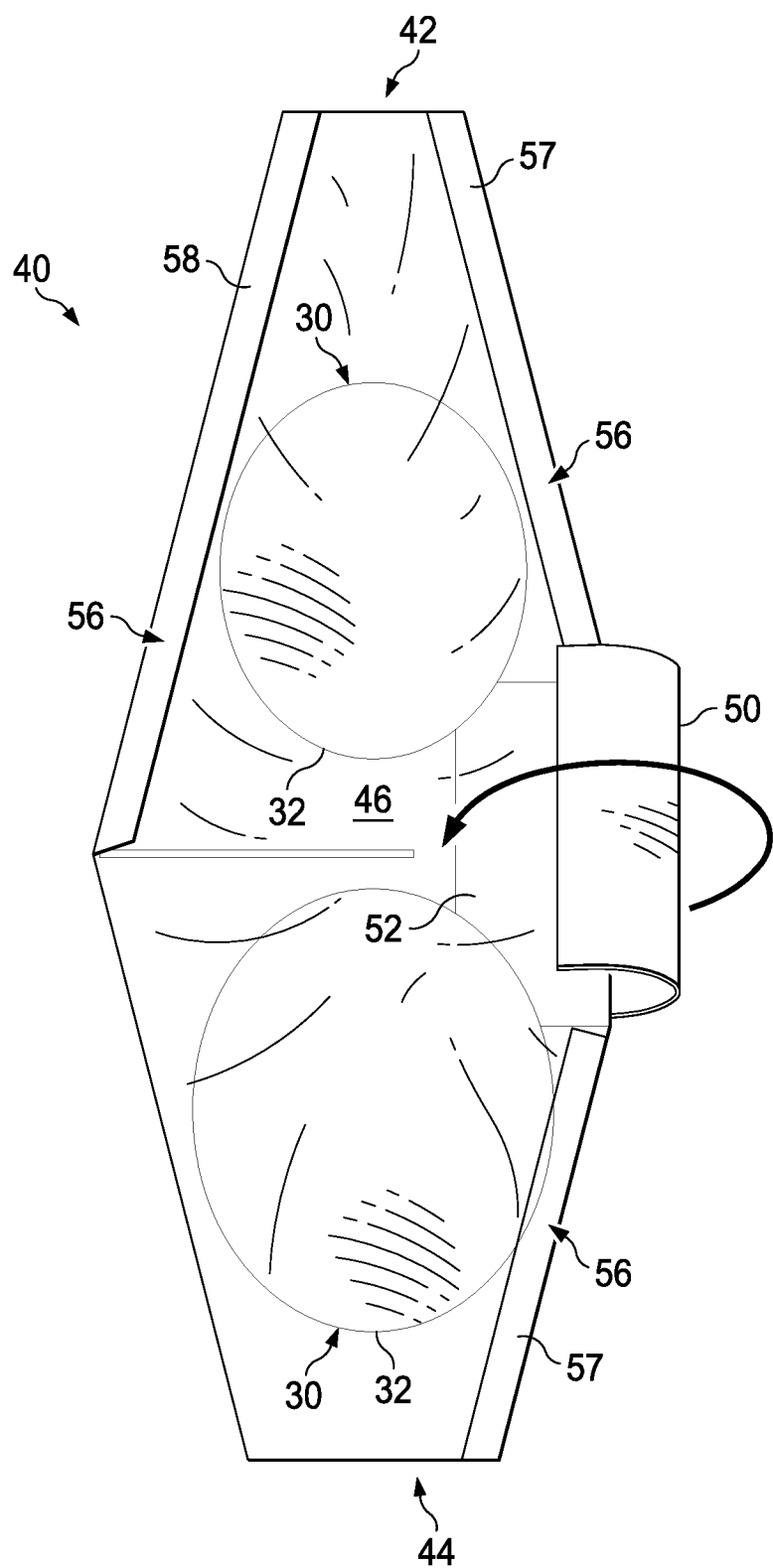

FIG. 4D: Top view of an asymmetrical bellow with the exterior tab being folded over the prosthesis opening.

Figure 5:
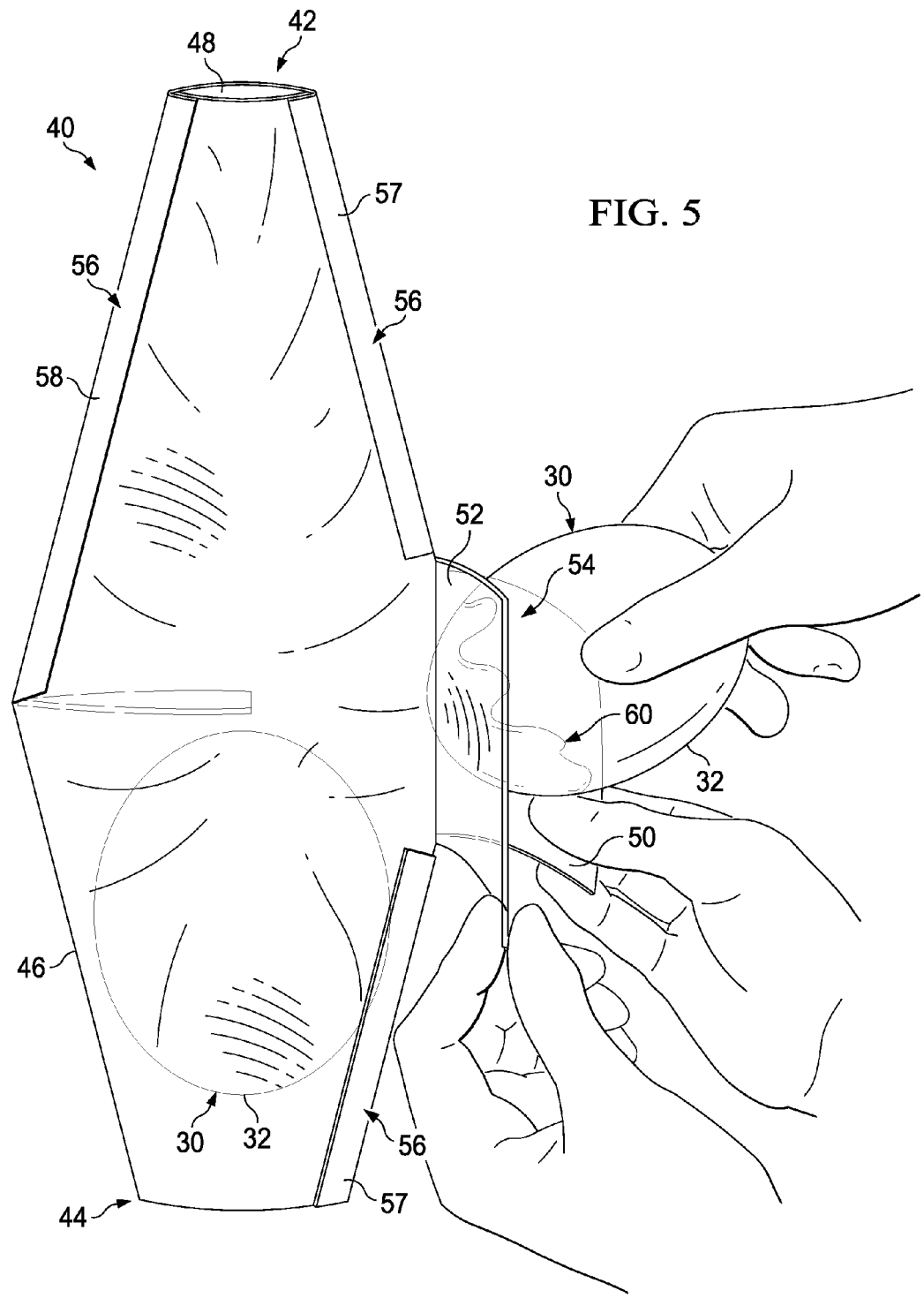

FIG. 5: Front perspective view of an asymmetrical bellow with an implant being inserted through the prosthesis opening, past the baffle, and into the small proximal end.

Figure 6:
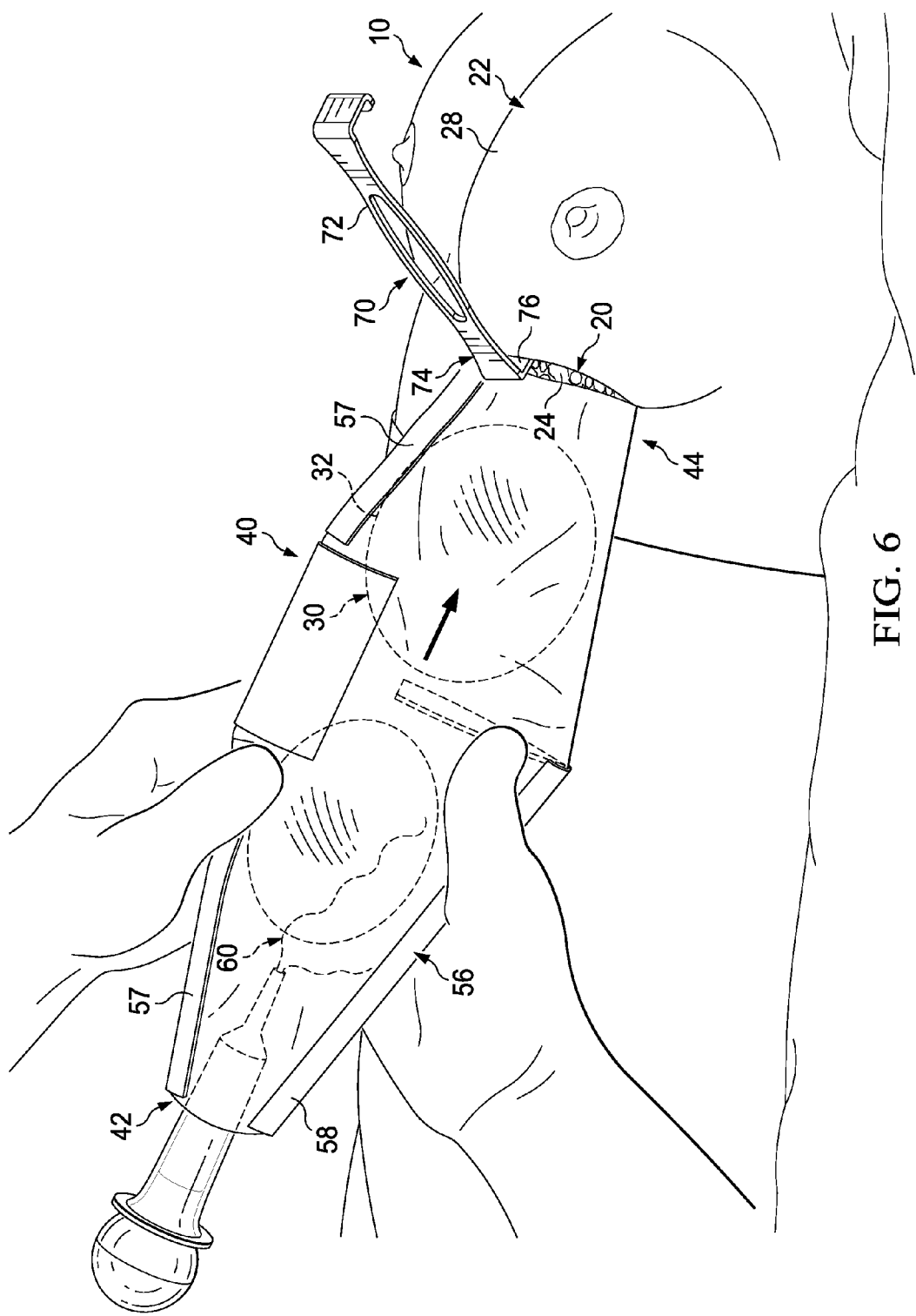

FIG. 6: Side perspective view of the operating team adding lubricant to the small proximal end of the asymmetrical bellow.

Figure 7A:
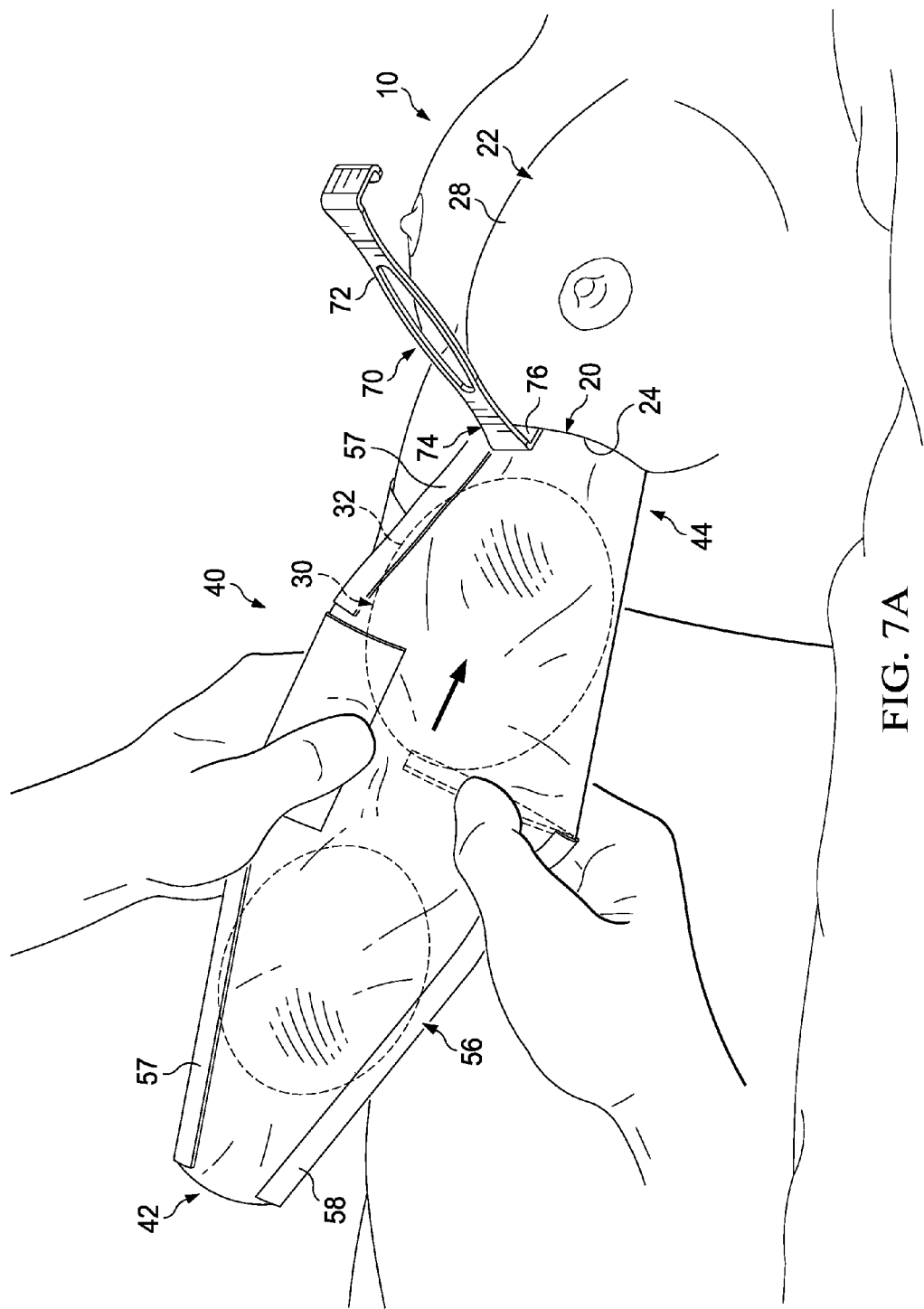

FIG. 7A: Left side perspective view of a baffled asymmetrical bellow with the large proximal end inserted into the left patient incision.

Figure 7B:
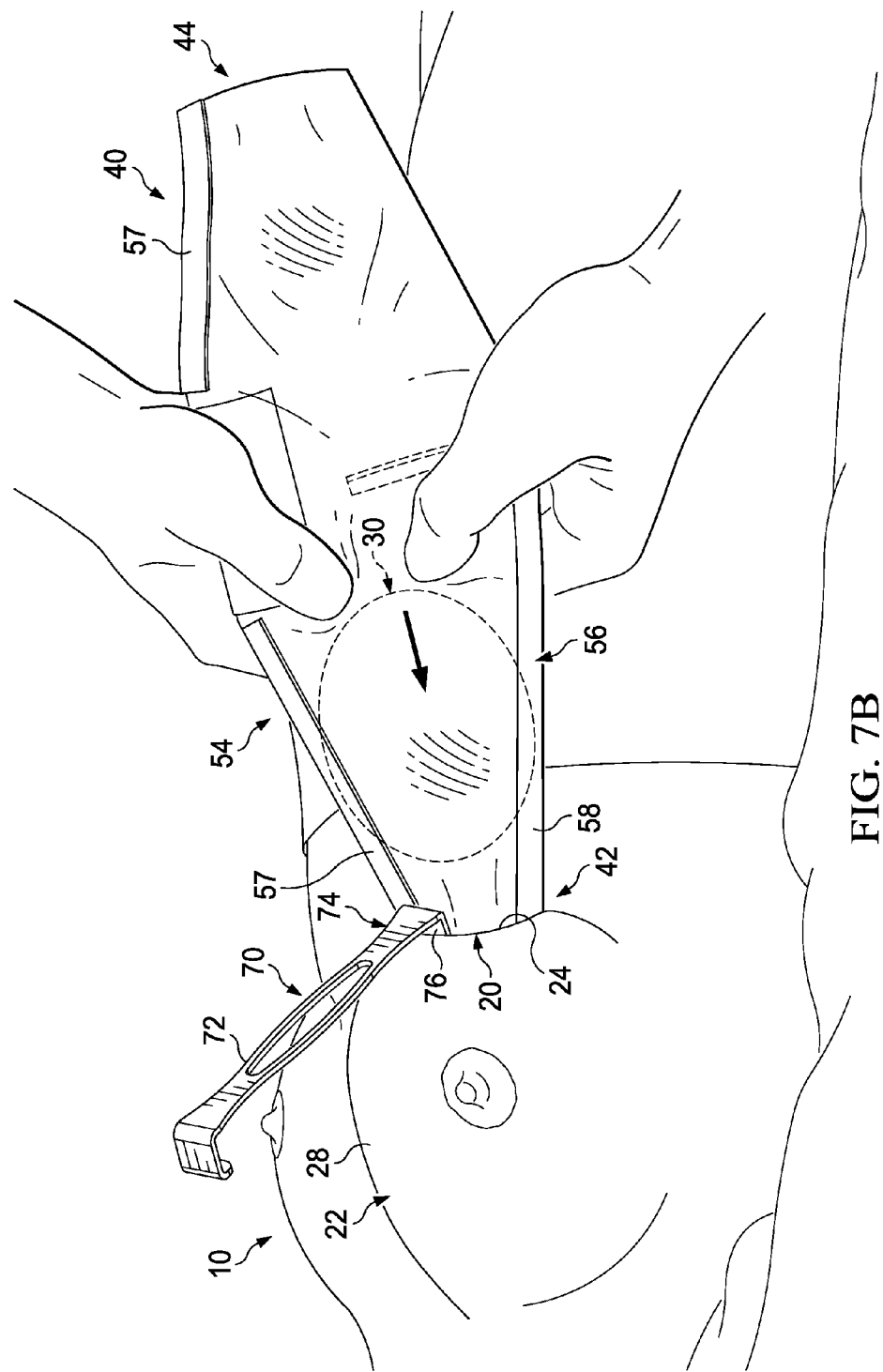

FIG. 7B: Right side perspective view of a rotated asymmetrical bellow with the small proximal end inserted into the right patient incision.

KEY TERMS distal: the most distant portion from the point of attachment to the body
inferior: closer to the feet
lateral: a position substantially located in any side of the longitudinal position of a patient's supine position
longitudinal: a lengthwise, or the longest, direction related to the patient's supine position
proximal: the closest portion from the point of attachment to the body
superior: closer to the head of the body

REFERENCE NUMERALS IN DRAWINGS 10 patient
20 patient's incision, opening
22 patient's breast
24 patient's implant pocket
28 patient's skin tissue
30 prosthesis
32 breast implant, implant
40 bellow device, bellow, asymmetrical bellow
42 small proximal end, small proximal opening
44 large proximal end, large proximal opening
45 proximal end
46 base fold
48 initial fold
50 exterior tab
52 internal tab
54 prosthesis opening
56 seal folds
57 tab-side seal tuck
58 abutted-side seal tuck
60 lubricant
70 retractor
72 retractor handle
74 retractor handle proximal end
76 retractor proximal end lip

DETAILED DESCRIPTION OF THE DRAWINGS

Referring to the drawings, in which like numerals represent like elements,

DETAILED DESCRIPTION OF THE DRAWINGS

Referring to the drawings, in which like numerals represent like elements,

FIGS. 1-2

Referring now to FIG. 1, the top side perspective view of a baffled asymmetrical bellow 40 manufactured with a sheet material such as plastic or a flexible, surgical-grade nylon. The plastic may be strengthened or reinforced with fibers. The asymmetrical bellow 40 may be clear, or semi-transparent, to allow observation of the prosthesis 30 moving from bellow 40 into the patient pocket 24.

The bellow 40 has three openings: a small proximal opening 42 for inserting a range of smaller implants into the incision 20; a large proximal opening 44 for insertion of a range of larger implants into the patient's incision 20; and a prosthesis opening 54, surrounded by an exterior tab 50 and an internal tab 52, for inserting the prosthesis 30 into the asymmetrical bellow device 40. Each end 42,44 is considered to be proximal because the device 40 is rotated during surgery so that each end 42,44 is sequentially inserted in the patient's openings 20. FIG. 1 shows the tabs 50,52 located central to the small proximal end 42 and large proximal end 44 and the internal tab 52 pushed through the prosthesis opening 54, to prevent the implant from passing to the outside of the bellow device 40, and the exterior tab 50 folded over the prosthesis opening 54. The exterior tab 50 may be folded and held in place by friction or attached by glue, adhesive, heat bond, surgical tape or other coupling mechanism. While FIG. 1 shows both tabs 50,52 folded into the working position, the bellow exterior tab 50 and bellow internal tab 52 would initially be presented to the surgeon with both tabs 50, 52 outside of the bellow 40 and surrounding the prosthesis opening 54. While the preferred embodiment shows different sized tabs 50,52 to distinguish the exterior tab 50 from the internal tab 52, the tabs 50, 52 may be of the same size.

Opposite the tabs 50,52, is a baffle 80 that is located inside the bellow and assembled to the initial fold 48 and based fold 46. The baffle bisects the small proximal end 42 and the large proximal end 44 to prevent the smaller-sized range of breast implants 32 from inadvertently slipping through the large proximal end 44. The baffle 80 is positioned in the middle of prosthesis opening 54 and extends from the abutted side of the bellow 40 toward the opening 54. The baffle 80 may also be positioned closer to the small proximal end 42 to allow the large implant to be placed inside the bellow 40. The baffle 80 may extend part way to the prosthesis opening 54, to the edge of the opening 54 or may be extend outside the opening 54. The baffle 80 may be of the same material as the bellow 40 or may be porous to allow lubricant 60 to pass easily from one chamber to the other. In practice, the nurse would hold open the tabs 50,52 while the surgeon places one implant through the prosthesis opening past the baffle 80 and to one side of the baffle 80.

The asymmetrical bellow 40 is assembled using the seal tucks 56 which comprise two (2) tab-side seal tucks 57, and one (1) abutted-side seal tuck 58. In a preferred embodiment, the assembly may be done prior to packaging and shipping to the surgeon. In an alternate embodiment, the seal tucks 56 and baffle 80 are sealed to the base fold 46 by the patient's 10 operating team. See FIG. 4B for additional illustration of the assembly using the seal tucks 56.

The bellow 40 prevents the breast implant 32 from touching the patient's skin tissue 28, prevents one proximal end 42,44 from being used in both incisions 20, and prevents damage to the implant 32 during the implant 32 insertion. The asymmetrical bellow 40 may be manufactured to accommodate any breast implant 32 shape, volume, and diameter. Each proximal end 42,44 would be sized to deliver a different range of implant 32 sizes and separated by a baffle 80. The manufacturer may also require or suggest two specific skin incision 20 lengths to allow insertion of the implant through the bellow 40 into the incision 20. The specifications take the burden off the surgeon to try to make shorter incisions 20.

While the preferred embodiment of the asymmetrical dual proximal end insertion bellow would have each end 42,44 used in a single operation, the manufacturer may elect to ship a single asymmetrical device 40 for operations with the same size implants. In this latter embodiment, the surgeon would use one proximal end 42,44 for the insertion of two implants 32.

FIG. 2 shows a bottom view of the manufactured version of the bellow 40 once the bellow fold 48 is folded over the base fold 46 along the abutted seam and the three seal tucks 56 are adhered to the base fold 46. The manufactured bellow 40 comprises the initial fold 48 partially sealed on the periphery to the base fold 46 so that it leaves a baffle 80, a small proximal opening 42, a large proximal opening 44, a bellow prosthesis opening 54, a bellow exterior tab 50 and a bellow internal tab 52. The large proximal end 44 is parallel to, and larger than, the device's 40 small proximal end 42.

FIGS. 3-4D

Turning to FIG. 3, the illustration depicting a perspective view of an unassembled bellow device 40. The asymmetrical bellow 40 form comprises two simple, convex, irregular hexagons folds 46, 48 bisected by a baffle 80 with opposing prosthesis insertion tabs 50, 52. In a preferred embodiment the tabs 50,52 are located centrally and opposing the abutted sides of the manufactured bellow 40. In a preferred embodiment, as shown in FIGS. 3-4D, the base fold 46 is manufactured abutted against the initial fold 48 along either edge opposing the tabbed side of the folds 46,48. In a second embodiment the initial fold 48 and base fold 46 would be separately manufactured and assembled together at a later stage.

In the preferred embodiment, the bellow 40 would be folded along an abutted edge and manufactured with three seal tucks 56 along:
  a. initial fold's 48 abutted-side edge from the abutment to the proximal end 42,44;
  b. initial fold's 48 tab-side edge from the exterior tab 50 to the small proximal end 42;
  c. initial fold's 48 tab-side edge from the exterior tab 50 to the large proximal end 44.

In the second embodiment, the bellow 40 would be manufactured with separated initial fold 48 and base fold 46, stacked over each other and assembled with four seal tucks 56 along:
  a. initial fold's 48 abutted-side edge from the abutment to the small proximal end 42;
  b. initial fold's 48 abutted-side edge from the abutment to the large proximal end 44;
  c. initial fold's 48 tab-side edge from the exterior tab 50 to the small proximal end 42;
  d. initial fold's 48 tab-side edge from the exterior tab 50 to the large proximal end 44.

The bellow seal tucks 56 may be folded over the opposing fold 46, 48 and attached by glue, adhesive, heat bond, surgical tape or other coupling mechanism. The baffle 80 may additionally be attached to the initial fold 48 and base fold 46 with glue, adhesive, heat bond, surgical tape or any other coupling mechanism.

In another embodiment, the seal tucks 56 may be replaced with a simple seam along the edges to bind the initial fold 48 and based fold 46 with glue, adhesive, heat bond, surgical tape or other coupling mechanism.

FIGS. 4A to 4D show the assembly of the asymmetrical bellow 40. In FIG. 4A, the pattern is folded along the abutted edge so that base fold 48 and initial fold 46 are stacked over each other with the tabs 50, 52 pointing in the same direction. The baffle 80 is attached to the base fold 46 and initial fold 48.

Then in FIG. 4B, the seal tucks 56 are folded over the opposing fold 46, 48 and sealed to the opposing fold 46, 48 with any desired manufacturing sealing technique.

With the breast implant 32 in place inside the asymmetrical bellow 40 on one side of the baffle 80, FIG. 4C, the internal tab 52 is pushed through the prosthesis opening 54. The internal tab 52 prevents the implant 32 from inadvertently ejecting through the prosthesis opening 54 during the operation.

In FIG. 4D, with the internal tab 52 inside the prosthesis opening 54, the exterior tab 50 may be pushed over the top surface of the opposing fold 46, 48. The exterior tab 50 may be sealed to the opposing fold 46, 48 with surgical tape, heat seal, instant glue, or other forms of seals. The adhered seal 50 opposes the prosthesis opening 54 and joins the initial fold 48 and base fold 46.

FIGS. 5-7B

As illustrated in FIG. 5, in the preferred embodiment a liquid lubricant 60 surrounds the breast implant 32 inside the bellow 40. A coating of surgical lubricant 60 may be used on the inner surface of the asymmetrical bellow 40. As an alternative, the bellow device 40 may be provided with a coating that becomes slick when wet. In still another alternative, the prosthesis 30 may be provided with a slick surface, such as a surgical lubricant 80. The surgeon also has the option of applying a lubricant 60 to the prosthesis 30 directly before inserting into the asymmetrical bellow 40. The lubricant 60 may also act as an antibiotic solution.

After lubrication, the breast implant 32 is inserted into the bellow device 40 by the surgeon and nurse. To do so, the nurse opens the bellow prosthesis opening 54 by separating the tabs 50, 52, and the surgeon slides the prosthesis 30 through the bellow prosthesis opening 54 and to either side of the baffle 80. The team would then fold the internal tab 52 into the bellow prosthesis opening 54 to prevent the breast implant 32 from moving back out of the opening 54. The exterior tab 50 may be left extended or folded over the opposing fold 46, 48. If desired, the exterior tab 50 may be sealed to the opposing fold 46, 48. In a preferred embodiment inserting the prosthesis 30 into the bellow device 40 would be completed prior to inserting the retractor 70 into the patient incision 20. However, a surgeon could perform this step while the bellow 40 is inserted in the incision 20. In a preferred embodiment the surgeon would insert one prosthesis 30 into the bellow device 40 at a time. However, a surgeon may insert both breast implants 32 before beginning the procedure.

In FIG. 6, the surgical team inserts lubricant 60 in the opposing opening 42,44 of the opening 42,44 inserted in the patient's incision 20. The liquid lubricant 60 surrounds the breast implant 32 inside the bellow device 40. An antibiotic solution may be used lubricant 60.

FIG. 7A shows the patient 10 positioned in a supine position prior to an incision 20 being made in the patient's skin tissue 28. In the figure, the incision 20 is cut in the left-side inferior breast 22 crease. With the incision 20 opened, the surgeon then forms a pocket 24 in one of two places under the breast 22: subglandular (between the breast 22 tissue and pectoralis muscle) or subpectoral (under the pectoralis muscle). The pocket 24 is sized to match the prosthesis 30. By manipulating the retractor handle 72, the retractor handle proximal end 74 and the retractor proximal lip 76 are inserted into the incision 20 to both retract the incision 20 and hold the incision 20 open.

The retractor 70 assembly comprises a handle 72 located in the center, retractor handle proximal end 74, and retractor handle proximal end lip 76. The retractor 70 may have various shapes and sizes to match the particular application or surgeon preferences. The handle 72 of the retractor 70 is bent or angled on the ends relative to the intermediate portion. The proximal end 74 of the retractor 70 has a lip 76 that is angled relative to the end 74. The retractor 70 is made of metal, such as stainless steel but may also be manufactured in a surgical plastic.

The retractor proximal end 74 is structured and arranged to be inserted through the incision 20 into a pocket 24 of a patient 10. The proximal end lip 76 helps maintain the proximal end 74 of the retractor 70 beneath skin tissue 28 of a patient 10.

The retractor 70 extends laterally from the asymmetrical bellow 40, so as not to interfere with the surgeon manipulating the bellow 40, with the proximal ends of the retractor 74 and proximal end lip 76 inserted into the incision 20 and located under the skin tissue 28 and moved to retract the incision 20. The proximal end 42,44 of the bellow 40 may be lubricated with a lubricant 60 and inserted into the open incision 20.

The asymmetrical bellow 40, distal to the incision 20, is squeezed and/or twisted to force the prosthesis 30 toward the proximal end 42,44 of the bellow device 40 and into the pocket 24. The prosthesis 30 deforms to fit through the proximal opening 44.

Once the prosthesis 30 is located inside the pocket 24, the retractor 70 is removed from the incision 20, followed by the bellow 40. The incision 20 is then closed.

Finally, in FIG. 7B, showing a right-side of a patient, a retractor 70 is inserted in the second breast 22 incision 20 and moved to retract the incision 20. The asymmetrical bellow 40 is then rotated so a new proximal end 42,44 is introduced to the incision 20 of the second breast 22. This second proximal end 42,44 may be lubricated with a lubricant 60 and inserted into the open incision 20.

The asymmetrical bellow 40, distal to the incision 20, is squeezed and/or twisted to force the prosthesis 30 toward the second proximal end 42,44 of the bellow device 40 and into the pocket 24. The prosthesis 30 deforms to fit through the second proximal opening 42,44.

Once the prosthesis 30 is located inside the pocket 24, the retractor 70 is removed from the second incision 20, followed by the bellow 40. The second incision 20 is then closed.

If the asymmetrical bellow 40 is designed for reuse, they are subjected to sterilization procedures. If the bellow 40 is designed for single use, they are disposed of. An advantage of the asymmetrical bellow 40 and method is that the implant 32 and proximal openings 42,44 may be properly sized during manufacture with respect to each other so that the smallest breast implants 32 will fit through small proximal opening 42 and the larger range of implants 32 will be properly inserted through the large proximal opening 44. This allows the proper pressure to be applied to each range of implants 32 as they deform through the proximal ends 42,44.

The implant 32 is subject to damage if the implant 32 is mishandled. Possible mishandling includes subjecting the implant 32 to undue stresses or pressures, such as may be caused by attempting to squeeze the implant 32 through a proximal end 42 that is too small, and folding of the external silastic shell, internal fracture of the cohesive silicone gel. A surgeon may make an incision 20 in the patient 10 that is too small for the implant 32 and thus too much force is required to squeeze the implant 32 into the pocket 24. With this bellow device 40, the implant 32 is protected from damage by the provision an adequate skin incision length and of the properly sized proximal end 44. The major complication with implants 32 is capsular contracture thought to be due to sub-clinical infection. Sub-clinical infection is most likely caused by pushing the implant 32 through the skin incision 20, dragging natural skin 28 bacteria (still present after proper skin 28 preparations) into the pocket 24 surgically created for the implant 32. Use of this device 40 prevents the implant 32 from coming in contact with the skin tissue 28 during the insertion process.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the invention have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the invention. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

Advantages

From the description above, a number of advantages become evident for the "Asymmetrical Dual Proximal End Insertion Bellow." The present invention provides all new benefits for participating parties including manufacturers, patients and surgeons:
  a) allows manufactures to ship a single breast implant insertion device for a pair of asymmetrical implants;
  b) allows manufacturers to ship a single size bellow for all implant sizes;
  c) allows patient's a lower risk of complications;
  d) allows doctors to prevent contamination by skin bacteria, gross infection from using a proximal end twice, resulting in infection and/or capsular contracture;
  e) allows doctors to eliminate the step of trimming the insertion device;
  f) allows doctors to eliminate damage to the implant during the insertion process;
  g) allows doctors a simplified insertion process;
  h) speeds the implant insertion surgery.

The invention claimed is:

1. An apparatus for inserting a prosthesis through an incision into a surgical pocket, comprising: a bellow formed of two convex, irregular hexagon folds with opposing tabs; a baffle assembled between the initial fold and base fold; an initial fold abutted to a base fold along the sides opposing the tabs; the initial fold folded over the base fold along the abutted edge; an abutted-side seal tuck from the abutment to the proximal end; a tab-side seal tuck from the tab to the small proximal end; a tab-side seal tuck from the tab to the large proximal end;
  whereby an asymmetrical bellow is formed with a bellow prosthesis opening, two proximal openings, and a baffle.

2. An apparatus for inserting a prosthesis through an incision into a surgical pocket, comprising: a bellow formed of two convex, irregular hexagon folds with opposing tabs; a baffle assembled between the initial fold and base fold; an initial fold abutted to a base fold along the sides opposing the tabs; the initial fold folded over the base fold along the abutted edge; an abutted-side seal tuck from the abutment to the proximal end; a tab-side seal tuck from the tab to the small proximal end; a tab-side seal tuck from the tab to the large proximal end;
  whereby an asymmetrical bellow is formed with a bellow prosthesis opening, two proximal openings, and a baffle.

3. An apparatus for inserting a prosthesis through an incision into a surgical pocket, comprising: a bellow formed of two convex, irregular hexagon folds with opposing tabs; a baffle assembled between the initial fold and base fold; an initial fold abutted to a base fold along the sides opposing the tabs; the initial fold folded over the base fold along the abutted edge; an abutted-side seam tuck from the abutment to the proximal end; a tab-side seal seam from the tab to the small proximal end; a tab-side seal seam from the tab to the large proximal end;
  whereby an asymmetrical bellow is formed with a bellow prosthesis opening, two proximal openings, and a baffle.

* * * * *